(12) United States Patent
Wright et al.

(10) Patent No.: US 6,931,951 B2
(45) Date of Patent: Aug. 23, 2005

(54) MECHANICAL DEVICE WITH SIMULATED SKIN SUBSTRATE

(75) Inventors: Audra S. Wright, Woodstock, GA (US); Martha L. Tate, Atlanta, GA (US); Nancy H. Puckett, Roswell, GA (US); Andrea S. Wulz, Roswell, GA (US); Susan C. Paul, Alpharetta, GA (US); Jason C. Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/324,884

(22) Filed: Dec. 20, 2002

(65) Prior Publication Data

US 2004/0118225 A1 Jun. 24, 2004

(51) Int. Cl.$^7$ ............................................... G01N 15/08
(52) U.S. Cl. ............................. 73/866.4; 73/38; 73/73; 73/159
(58) Field of Search ............................ 73/38, 73, 74, 73/76, 159, 865.6, 866

(56) References Cited

U.S. PATENT DOCUMENTS

| | | | | |
|---|---|---|---|---|
| 839,431 A | * | 12/1906 | Smith | 223/67 |
| 1,561,285 A | * | 11/1925 | Sesler | 73/73 |
| 2,545,281 A | * | 3/1951 | Hunt | 73/73 |
| 3,284,947 A | * | 11/1966 | Dahl | 446/374 |
| 3,341,394 A | | 9/1967 | Kinney | |
| 3,502,538 A | | 3/1970 | Peterson | |
| 3,502,763 A | | 3/1970 | Hartmann | |
| 3,542,615 A | | 11/1970 | Dobo et al. | |
| 3,734,362 A | * | 5/1973 | Arthur | 223/68 |
| 3,952,584 A | * | 4/1976 | Lichstein | 73/73 |
| 4,041,203 A | | 8/1977 | Brock | |
| 4,257,188 A | * | 3/1981 | Barker | 446/295 |

(Continued)

FOREIGN PATENT DOCUMENTS

| | | | | |
|---|---|---|---|---|
| CA | 803714 | | 1/1969 | |
| DE | 719491 C | * | 4/1942 | |
| FR | 958776 | * | 3/1950 | |
| FR | 1027757 | * | 5/1953 | |
| FR | 1258883 | * | 8/1961 | |
| FR | 2452752 | * | 11/1980 | |
| GB | 2272182 A | * | 5/1994 | ........... B29C/69/00 |
| JP | 61004909 | * | 1/1986 | |
| SU | 1306260 | * | 4/1987 | |

OTHER PUBLICATIONS

U.S. Appl. No. 10/324,834, filed Dec. 20, 2002.

U.S. Appl. No. 10/324,605, filed Dec. 20, 2002.

U.S. Appl. No. 10/324,365, filed Dec. 20, 2002.

Fan et al., U.S. Pat. Pub. No. 2002/0191669, entitled *Thermal Manikin*, published Dec. 19, 2002.

Primary Examiner—Hezron Williams
Assistant Examiner—David A. Rogers
(74) Attorney, Agent, or Firm—Dority & Manning, P.A.

(57) ABSTRACT

An apparatus for evaluating a material is provided. In one aspect, the apparatus is an adjustable artificial arm for transmitting fluid into the material. An artificial skin, for example, is removably attached to the artificial arm, and the material is placed over the artificial skin. The fluid is insulted into the material proximate the artificial skin. The artificial skin is evaluated for wetness or dryness to prescreen the material. In another aspect, an artificial torso is provided through which fluid is transmitted and insulted into the material for evaluation.

13 Claims, 6 Drawing Sheets

U.S. PATENT DOCUMENTS

| | | | | |
|---|---|---|---|---|
| 4,261,113 A | * | 4/1981 | Alderson | 434/274 |
| 4,340,563 A | | 7/1982 | Appel et al. | |
| 4,357,827 A | * | 11/1982 | McConnell | 73/73 |
| 4,417,401 A | * | 11/1983 | Aisaka et al. | 33/512 |
| 4,701,132 A | * | 10/1987 | Groesch et al. | 434/274 |
| 4,720,415 A | | 1/1988 | Vander Wielen et al. | |
| 4,773,865 A | * | 9/1988 | Baldwin | 434/268 |
| 4,932,919 A | * | 6/1990 | Shapero | 446/374 |
| 5,018,977 A | * | 5/1991 | Wiley et al. | 434/274 |
| 5,066,259 A | * | 11/1991 | Acker | 446/385 |
| 5,067,924 A | * | 11/1991 | Munter | 446/320 |
| 5,361,627 A | * | 11/1994 | Levesque | 73/73 |
| 5,419,729 A | * | 5/1995 | Gross | 446/183 |
| 5,425,265 A | * | 6/1995 | Jaisinghani | 73/38 |
| 5,518,436 A | * | 5/1996 | Lund et al. | 446/180 |
| 5,566,867 A | * | 10/1996 | Goray | 223/66 |
| 5,630,745 A | * | 5/1997 | Yeh | 446/374 |
| 5,913,708 A | * | 6/1999 | Gross | 446/385 |
| 6,004,136 A | * | 12/1999 | Ehrenpreis | 434/262 |
| 6,015,935 A | * | 1/2000 | LaVon et al. | 604/378 |
| 6,107,537 A | * | 8/2000 | Elder et al. | 604/364 |
| 6,152,906 A | * | 11/2000 | Faulks et al. | 604/385.01 |
| 6,298,714 B1 | | 10/2001 | Courtray | |
| 6,413,142 B1 | * | 7/2002 | Weastler | 446/320 |
| 6,446,495 B1 | * | 9/2002 | Herrlein et al. | 73/73 |
| 6,464,557 B1 | * | 10/2002 | Ohba et al. | 446/391 |
| 6,503,525 B1 | * | 1/2003 | Mayberry et al. | 424/402 |
| 6,534,074 B2 | * | 3/2003 | Krzysik et al. | 424/402 |
| 6,557,398 B2 | * | 5/2003 | Lindmark et al. | 73/73 |
| 2002/0191669 A1 | | 12/2002 | Fan et al. | |

* cited by examiner

MECHANICAL DEVICE WITH SIMULATED SKIN SUBSTRATE

BACKGROUND OF THE INVENTION

Absorbent articles such as diapers, adult incontinence garments, feminine care products, child training pants, pullups, bandages, gloves and similar products that directly contact skin are well known. A disposable absorbent article is typically composed of a top layer that is adjacent to a user's body and a back layer that faces the clothing of the user. An absorbent material is located between the top layer and the bottom layer. The top layer permits a liquid from the user to move through the top layer toward the back layer. The back layer does not allow liquid to be transferred from the inside of the absorbent article onto the user's clothing. The absorbent material absorbs the liquid and keeps the skin dry.

During normal operation after a fluid is discharged from a user, the fluid will flow through the top layer and be absorbed by the absorbent material. The absorbent material is designed to absorb, redistribute, and store the fluid until the absorbent article is discarded. In some instances, however, fluid may return from the absorbent material to once again contact the user's skin. Fluid return can occur, for instance, if the absorbent material cannot sufficiently absorb the fluid due to the composition of the absorbent material. Unabsorbed liquid undesirably results in over-hydration of the contacted skin and in turn, increases a chance of skin irritation to the user. In addition to being an irritant, excessive moisture on the user's skin can cause, among other things, the growth of microorganisms that can lead to the onset of rashes or infection.

Various tests exist for measuring performance and suitability of absorbent materials to prevent the foregoing problems. Known tests include capacitance, conductance, electrical impedance, gravimetric, and/or evaporative or Trans-Epidermal Water Loss (TEWL) evaluations. Typically, these tests measure fluid absorbency, fluid leakage, and other criteria of the materials for use in absorbent articles.

The Adult Forearm Test or "armband" test, by way of specific example, is conventionally used to evaluate the effectiveness of disposable diapers to keep the skin dry. One variation of the armband test uses pre-loaded patches from diapers placed on an adult volar forearm. Changes in skin surface hydration are measured by evaporimetry or TEWL evaluation. Differences in skin surface hydration between cloth diapers and disposable paper diapers have been noted using this armband test variant.

Another armband test uses an intact diaper wrapped around the forearm. Physiological saline is injected into the diaper at a rate and volume that represent normal urination by a child. Post-occlusion measurements are made after one hour, and measurements of skin hydration are made by computerized evaporimetry or by electrical conductance.

BRIEF SUMMARY OF THE INVENTION

In general, the present invention provides an evaluation apparatus to evaluate materials quickly, efficiently and cost effectively. The evaluation apparatus acts as a pre-screening tool to bench test materials for diaper, childcare, feminine care, adult care, health care, competitive and other products without human subjects. The component parts of the invention are simple, reliable, and economical to manufacture and use. Also, used herein, the terms "simulated," "virtual," "artificial," "synthetic" and like terms are used interchangeably to indicate manufactured materials or objects, and in the case of substrates, dissected or bioengineered skin samples, unless otherwise indicated.

In one aspect of the invention, a mechanical arm includes a Plexiglas®-type cylinder arranged to simulate an adult forearm for rapidly pre-screening and ranking a material for further evaluation, possibly on human subjects. The arm incorporates a fluid injection port to simulate a sweat gland, a pore, a body cavity, etc. and the like. A simulated skin substrate is placed on a portion of the arm proximate the fluid injection port. The material is wrapped about the simulated skin substrate and the fluid injection port. Saline or other simulated physiological fluid is insulted into the material. After a predetermined time, the material is removed and the skin is evaluated for dryness.

In another aspect of the invention, a silicone, neoprene or similar material is used to form a mechanical torso that simulates an infant. As used herein, the terms "torso", "mannequin" and like terms are used interchangeably to indicate simulated body parts, unless indicated otherwise. The mechanical torso incorporates a fluid injection port to simulate a sweat gland, a pore, a urethra and the like. A simulated skin substrate such as VITRO-SKIN™ is placed on a portion of the torso proximate the fluid injection port (e.g., on the front of the torso in a suprapubic area). The material is wrapped about the simulated skin substrate and the fluid injection port. Saline or other simulated physiological fluid is insulted into the material either automatically or manually by a fluid loading device. After a predetermined time, the material is removed and the skin is evaluated for dryness.

In a further aspect of the invention, a method is provided to measure differences between materials combination in product form for dryness. This method can be used to prescreen materials for TEWL.

The foregoing aspects of the present invention enable rapid pre-screening of material at relatively low cost by avoiding variables in a population of human subjects. Other aspects and advantages of the invention will be apparent from the following description and the attached drawings, or can be learned through practice of the invention.

BRIEF DESCRIPTION OF THE DRAWINGS

The above and other aspects and advantages of the present invention are apparent from the detailed description below and in combination with the drawings in which.

Figure 1:
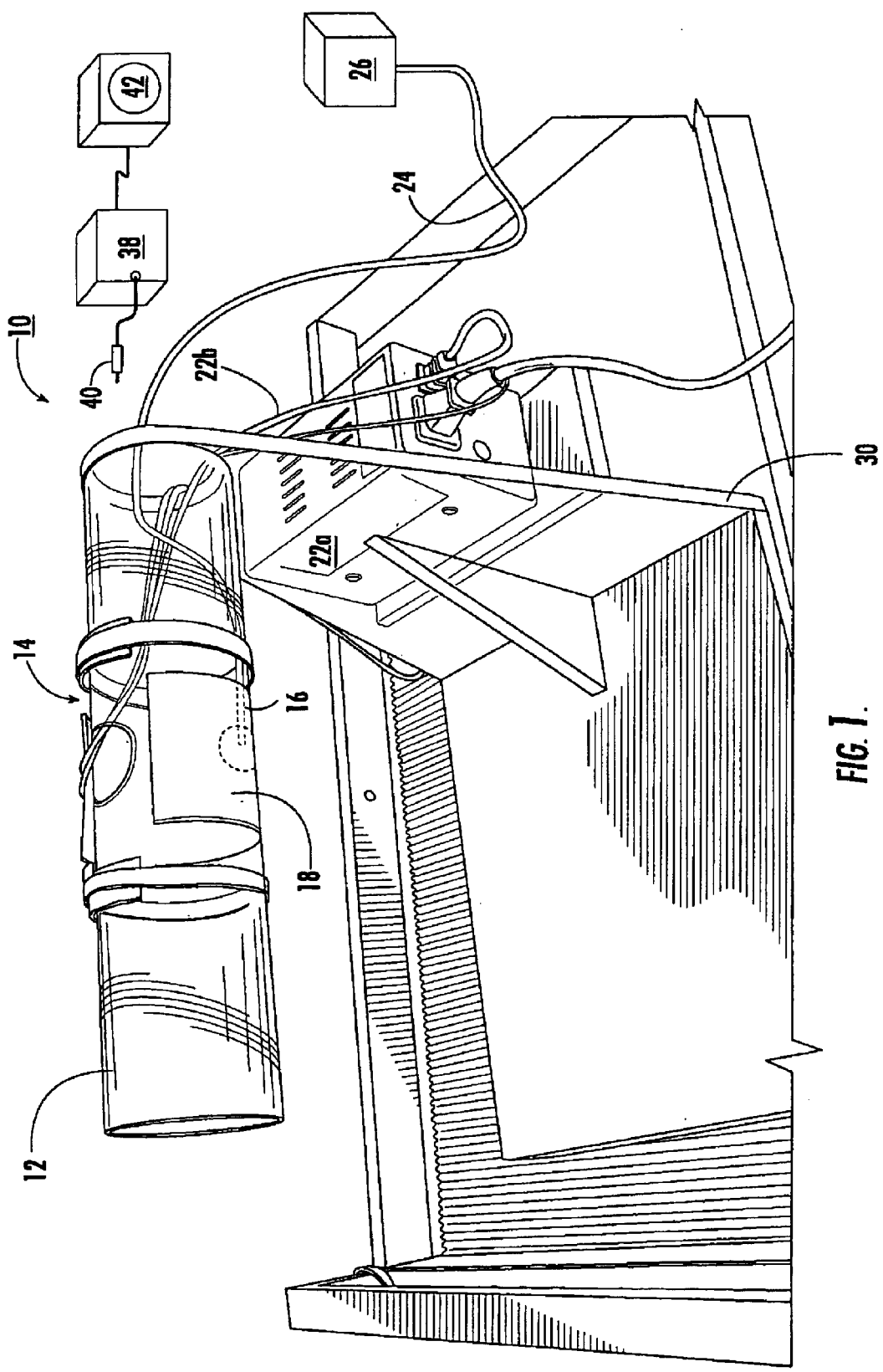
FIG. 1 is a perspective view of an apparatus in accordance with an aspect of the invention.

Repeat use of reference characters in the drawings and the detailed description is intended to represent same or analogous features or elements of the invention.

DETAILED DESCRIPTION OF THE DRAWINGS

Detailed reference will now be made to the drawings in which examples embodying the present invention are shown. The drawings and detailed description provide a full and detailed written description of the invention and the manner and process of making and using it, so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended Claims and their equivalents.

In general, the present invention is directed to an evaluation apparatus for quickly pre-screening and ranking products or materials without requiring human subjects. Once the materials are pre-screened or bench tested, a determination can be made as to which materials warrant additional testing and evaluation, possibly on human subjects. Materials include an absorbent material, disposable or non-disposable diapers, diaper systems, adult incontinence products, feminine products, nursing healthcare products, child training products, bandages, gloves, face masks, and similar disposable and non-disposable products that contact a consumer's skin. Additionally, the material can be a nonwoven polymer material, an airlaid material, a wet material, a dry material, a treated material, and disposable or non-disposable materials.

As broadly embodied in FIGS. 1–4, an evaluation apparatus 10 includes an object or arm 12 with an artificial (simulated) skin 32 attached to the arm 12. A material 36 is disposed about the skin 32, and a pump or fluid delivery device 26 is provided to insult the material 36 with a simulated physiological fluid 28 via the arm 12. The fluid 28 may be water, saline, natural or simulated menses fluid, urine, breast milk, or blood, a solution of 0.9% sodium chloride, a colored solution, an exudate or any suitable material for simulating human body fluids. The foregoing components facilitate skin dryness measurements, which can be conducted by capacitance, conductance, electrical impedance, gravimetric, Trans-Epidermal Water Loss (TEWL), and other evaluations to measure skin hydration and moisturization. Material evaluators are thus able to rapidly pre-screen materials without the need for human subjects as presently required, for instance, using the standard Adult Forearm Test. Further details of the evaluation apparatus 10 and its operation are discussed below.

Referring to FIG. 1, there is shown a perspective view of one embodiment of the evaluation apparatus 10 in which the arm 12 is attached to a base 30. The arm 12 can be adjustably attached to the base 30 to facilitate the TEWL measurements that are described below. In the example shown, the arm 12 is formed of a Plexiglas® material and is approximately 3¼ inches×13⅝ inches with a 10¼ inch circumference to simulate an adult female forearm. Although the exemplary arm 12 is made of Plexiglas® type, other materials such as acetyl plastic, an acrylic plastic, an elastomeric material, a high density polyethylene, a polymer, a metal, a glass, composite materials or similar moldable materials may be suitably used. Also, while the illustrated arm 12 is representative of a female forearm, it is not intended as a limitation of the invention. For example, the circumference of the arm 12 can be from about 3 inches to about 80 inches and can be adjusted electronically, hydraulically, pneumatically, manually, or otherwise in proportion to the material to be tested. For instance, the arm 12 may be adjusted to a circumference of about 3–5 inches to test a premature baby material, or to about 80 inches to test a large size adult undergarment.

FIG. 1 also shows a heater 18 wrapped around an attachment area 14 of the arm 12. Heating the skin 32 with the heater 18 facilitates correlation of the present invention to the conventional Adult Forearm Test in order to better support, for instance, advertising claims and to develop products. To simulate normal human skin temperature, the heater 18 is connected to a power source 22a via an electrical connection 22b as shown in FIG. 1. The heater 18 is heated from about 70° Fahrenheit (F.) to about 120° F. to heat the skin 32. More specifically, the heater 18 heats the skin 32 to about 85–99° F., usually to about 95° F., to emulate the normal human skin temperature, rather than the skin 32 remaining at an ambient room temperature. Thus, the TEWL measurements more closely reflect measurements that may derive from a human forearm. Further operation of the heater 18 and resulting TEWL measurements are described in the Exemplary Procedures and Exemplary Results sections below.

As shown in FIG. 1, the heater 18 can be fashioned from a flexible silicone rubber, neoprene, or other flexible material and is designed for removable attachment to the apparatus 10. In this aspect, the heater 18 has a heater hole 20 (see FIG. 3), which is 5/16 inch to simulate a normal urine load of a child. However, a plurality of heater holes having various other sizes may be utilized to simulate a variety of human age groups and bodily functions. Moreover, the arm 12 may be other shapes or anatomical parts such as a thigh, an upper arm and the like, and is not limited to the simulated, cylindrically shaped forearm as shown. Thus, the removable heater 18 can be sized to match any other simulated body part such as an infant's torso and may include one or more heater holes of various sizes.

A heater suitable for use with the exemplary arm 12 is a 3-inch×8⅛ inch rubber silicone Watlow 120 Volt (V) heater available from Watlow Electric Manufacturing Company of St. Louis, Mo. Other comparable heaters from other manufacturers may also be used for heater 18. It should also be understood that the heater 18 may be integrally formed, for instance, as heater elements within the evaluation apparatus 10 and is not limited to the illustrated wrappable heater 18. More specifically, the arm 12 can be a heatable silicone rubber in which a network of heating elements is embedded in the silicone rubber in order to simulate human skin temperature on a heating surface of the apparatus 10. Thus, in an alternative aspect of the invention, the arm 12 itself can be formed of a heat conductive metal, glass, rubber or other material that can be heated and not absorb fluid.

In one aspect of the invention, the fluid delivery device 26 of FIG. 1 is a syringe or similar device to manually inject the fluid 28. In another aspect, the fluid delivery device 26 may be a digital pump or a computer controlled pump, which delivers a predetermined amount of fluid 28 (see FIG. 3) through the arm 12. Although other pumps are available, a Masterflex® Computerized Water Pump, available from Cole-Parmer of Vernon Hills, Ill., is a suitable fluid delivery device 26. The Cole-Parmer Masterflex® Computerized Water Pump can be operated via a Windows® Linkable Instrument Network (WINLIN) software program to link multiple pumps and mixers in synchronized or unsynchronized sequences of operation. The WINLIN program also features:

Flow calibration by volume, weight or flow reference
   Multiple flow, volume and torque units
   Volumetrical or gravimetrical dispensing
   Constant or ramped flow/speed control A tubing or fluid tube 24 is also shown in FIG. 1 delivering the simulated physiological fluid 28 through a fluid injection port 16 in the arm 12 from the fluid delivery device 26. In this exemplary arrangement, the tube 24 is routed within the apparatus 10 to ensure, for instance, that the tube 24 is not disturbed by external forces. However, it is to be noted that the tube 24 can be arranged externally to the apparatus 10 without affecting its operation. The operation of the tube 24 is described in greater detail below.

FIG. 1 further illustrates a measuring device 38 with a stand-mounted or hand-held probe 40 that can be used to determine skin dryness, diaper pooling, skin saturation and the like by evaluating the skin 32 after insulting the material 36 with the fluid 28. By way of example, a DermaLab® Trans Epidermal Water Loss (TEWL) probe, developed by Cortex Technology, Denmark, available from cyberDERM, Inc., Media, Pa., is a suitable measuring device 38, although any comparable probe may be used. As briefly introduced, the arm 12 in an exemplary embodiment is adjustably attached to the base 30. Therefore, the arm 12 can be swiveled, rotated, retracted, extended, ratcheted, inclined, reclined or otherwise oriented for the probe 40 to contact the skin 32 without having to remove the skin 32 from the arm 12 to take TEWL measurements.

An electronic display unit or monitor 42 can be electronically attached to the measuring device 38 to display the TEWL measurements. The measuring device 38 and/or the monitor 42 can include recording capabilities to automatically save the TEWL measurements to a magnetic tape, hard drive, disc or the like. Further details of the testing protocol and operation of the apparatus 10 and the measuring device 38 are discussed below.

Figure 2:
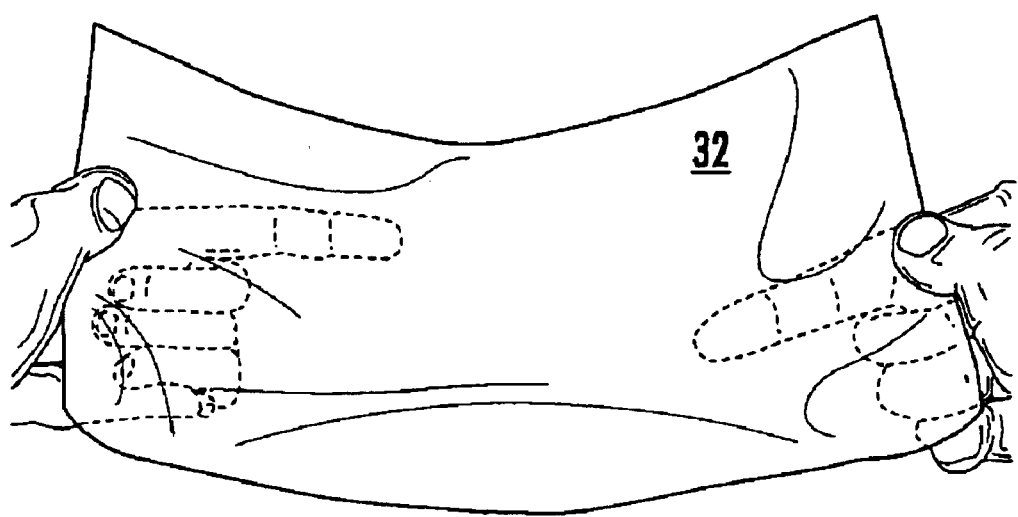
FIG. 2 is a perspective view of a portion of simulated skin in accordance with another aspect of the invention.

Referring to FIG. 2, a portion of the simulated skin 32 is shown. As introduced, after the material 36 is insulted with the fluid 28, the simulated skin 32, which is at least partially covered with the insulted material 36, is evaluated for wetness/dryness (e.g., TEWL) using the probe 40 of the measuring device 38 to prescreen the material 36.

A variety of simulated skin materials and products are suitable for use as simulated skin 32 to demonstrate the hydration and/or moisturization properties of personal care products, diapers and the like. Examples include but are not limited to VITRO-SKIN™ and VITRO-CORNEUM® available from IMS Inc., Milford, Conn.; TEST SKIN™ II from Organogenesis Inc., Canton, Mass.; SKINETHIC® from Skinethic Tissue Culture Laboratories, Nice, France; EpiDerm™ simulated human skin from MatTek Corporation, Ashland, Mass.; a medical grade collagen film; a collagen in a sausage casing; a cellulose film; a custom prepared chamois available from Acme Sponge and Chamois Company, Tarpon Springs, Fla.; a cultured skin or bioengineered substrate; a living/preserved skin sample from animal models such as but not limited to a pig, a monkey and a human cadaver; and similar materials.

By way of example, VITRO-SKIN™ substrate contains protein and lipid components and is designed to have topography, pH, critical surface tension and ionic strength that mimic human skin. Its consistent topography ("N-19 topography") and wetting properties across each sheet of VITRO-SKIN™ are optimized to mimic relatively smooth skin found on the human back. Thus, testing done on VITRO-SKIN™ is generally more reproducible than that performed on variable human skin samples due to the consistent topography of VITRO-SKIN™. In comparison, VITRO-CORNEUM® is a collagen-based substrate with properties similar to human stratum corneum. VITRO-CORNEUM® substrate is designed to simulate the thickness, visco-elasticity and surface properties of human stratum corneum; i.e., the outer layer of epidermis of primarily dead skin cells.

Another suitable simulated skin substrate is collagen in a sausage casing. Collagen is a cost-effective alternative for pre-screening materials 36 since collagen does not have to be handled and stored as a biological sample. An exemplary collagen is available from NATURIN GmbH, Weinhein, Germany, under the designation of COFF12224. COFF12224 is a collagen film having a basis weight of about 28 g/m². Another exemplary collagen film is available from Devro, Inc, Geneva, Ill., under the designation of Cutisin™.

Figure 3:
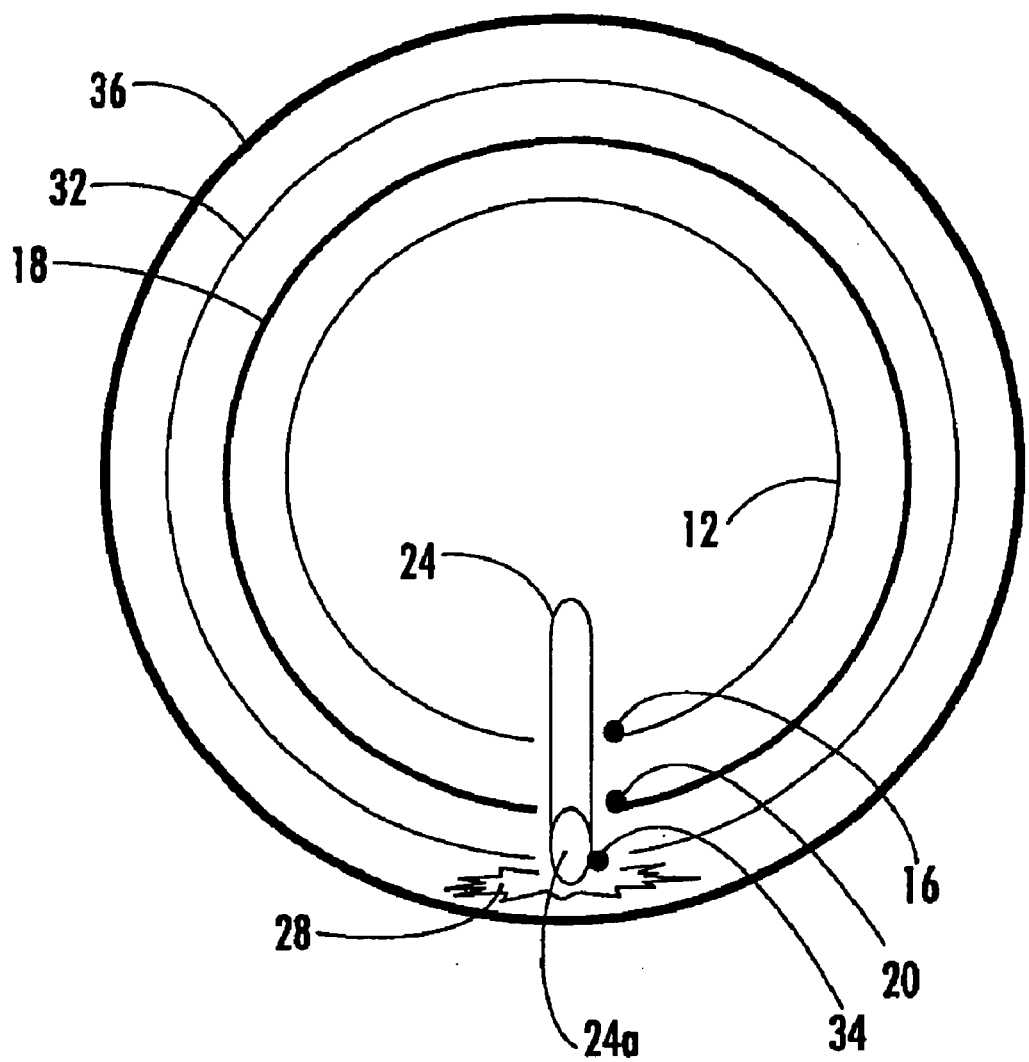
FIG. 3 is an end view of a mechanical arm in accordance with a further aspect of the invention.

With reference to FIG. 3, the heater 18 is attached in the attachment area 14 (see FIG. 1) of the arm 12 as previously discussed. The fluid tube 24 is inserted through a fluid injection port 16 in the arm 12. In this example, the fluid injection port 16 is about 0.25 inches but may be up to about 1 inch in circumference. The fluid tube 24 is also shown at least partially inserted through the heater hole 20, which is substantially aligned with the injection port 16. This arrangement allows the fluid 28 to be insulted into the material 36 as described below. However, it is to be noted that fluid 28 can be insulted into material 36 in a variety of arrangements. For instance, the material 36 can be preloaded with the fluid 28 before placing the material 36 on the arm 12. Alternatively, after the material 36 is placed on the arm 12, the fluid 28 may be insulted in the material via a syringe (not shown); i.e., a hand-fed or off-line fluid loading device.

FIG. 3 further shows the simulated skin 32 attached to the heater 18 to be heated to the human skin temperature previously described. The fluid tube 24 is placed near or through the skin 32, which may have a skin opening 34. In this example, the fluid tube 24 (and skin opening 34 if provided) is also aligned substantially with the heater hole 20. The injection port 16, heater hole 20, skin opening 34 and an insult source (outlet) 24a of the tube 24 simulate a human urethra. Thus, these elements cooperate to insult the fluid 28 into the material 36, such as a diaper, when the material 36 is placed about the skin 32.

As suggested with respect to FIG. 1 above, a fluid loading protocol is used to simulate a child's model urine load to insult the material 36 with fluid 28. This protocol is described in greater detail under the following Exemplary Procedures section. However, it is to be understood that the outlet 24a, heater hole 20 and/or skin opening 34 can vary in size and number to simulate tear ducts, pores, a body cavity, a urethra, and similar openings. Additionally, various other fluid loading protocols can be applied to model infant urination, adult perspiration, menses, synthetic breast milk and blood such as bovine blood or other fluid excretions.

Figure 4:
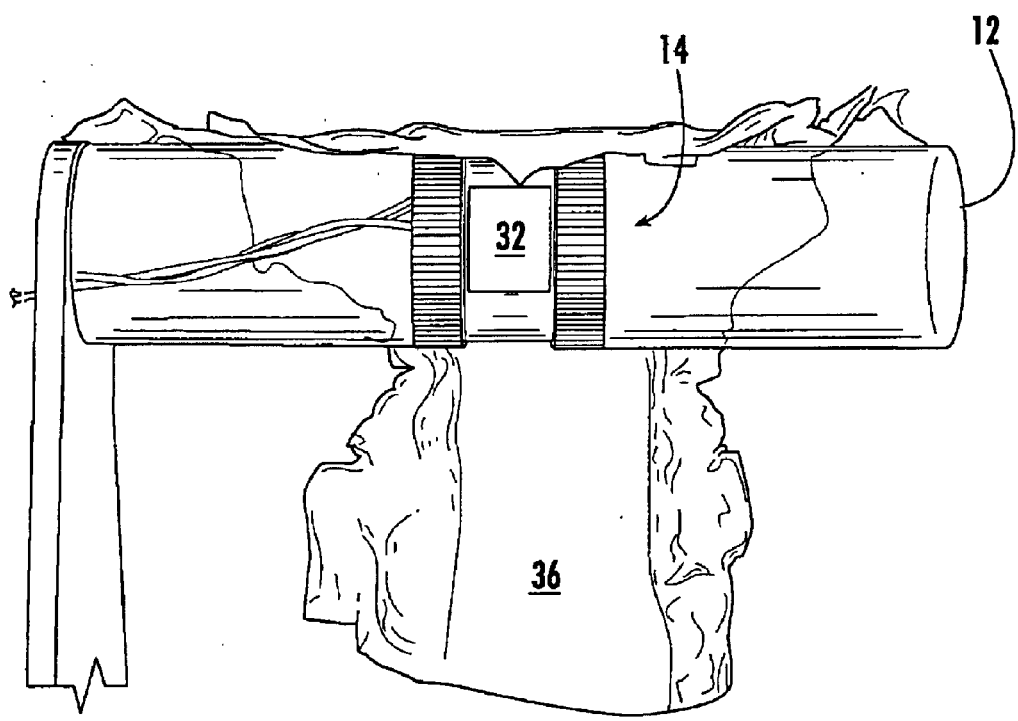
FIG. 4 is a perspective view of the simulated skin and a material attached to the mechanical arm.

Moreover, although skin 32 is shown wrapped around the heater 18 in FIG. 3, it is to be understood that the skin 32 may be a small patch or square of skin 32 relative to the heater 18 as seen in FIG. 4. The small patch of skin 32 is placed at pre-selected distances from the heater hole 20 and outlet 24a. For example, research has shown that 6 centimeters (cm) is an advantageous distance from the insult source 24a to the skin 32. Using VITRO-SKIN™ as the skin 32, the inventors have found through placing the skin 32 at various locations on the arm 12 that fewer differences are detectable when the simulated skin 32 is placed closer to the insult source 24a. Stated another way, although distances of about zero cm to about 12 cm are feasible, TEWL measurements may undesirably vary or be difficult to differentiate when the skin 32 is too close to the insult source 24a and a transmission or surge area of the fluid 28.

It is notable that the VITRO-SKIN™ is sensitive to the environment under the material 36 when starting from a dry state (preconditioned at 40% RH). When the VITRO- SKIN™ becomes flooded or saturated with fluid 28, high TEWL readings result, which reflect no differences between materials 36. Further, if the VITRO-SKIN™ is used without rinsing it, the TEWL values are stable for at least two uses. However, if the VITRO-SKIN™ is rinsed between uses and reconditioned to test humidity, the rinsed VITRO-SKIN™ is not re-usable. Important components such as glycerin may be washed off and negatively impact test results. Accordingly, at least if VITRO-SKIN™ is utilized as the skin 32, rinsing is not recommended.

With reference to FIG. 4, the heater 18 is shown attached to the arm 12 in a conventional manner such as by a hook and loop fastening system, tape or the like. The electrical connection 22b and fluid tube 24 are routed within the arm 12, which is hollow in this example, although one or both of the electrical connection 22b and fluid tube 24 can be routed externally if desired. The fluid tube 24 is then inserted through the fluid injection port 16 and heater hole 20 as described with respect to FIG. 3 above.

In operation, the material 36 (seen partially detached for clarity in FIG. 4) is securely wrapped about the arm 12 to at least partially cover the heater 18 and the skin 32. The fluid delivery device 26 delivers the fluid 28 through the tube opening 24a of the fluid tube 24 into the material 36 for TEWL or other evaluation. After a predetermined time, the arm 12 can be swiveled about the base 30 to evaluate the skin 32, or the skin 32 can be removed and measured remotely from the arm 12. Operation of the apparatus 10 is further described in the following protocols and experiments.

Figure 5:
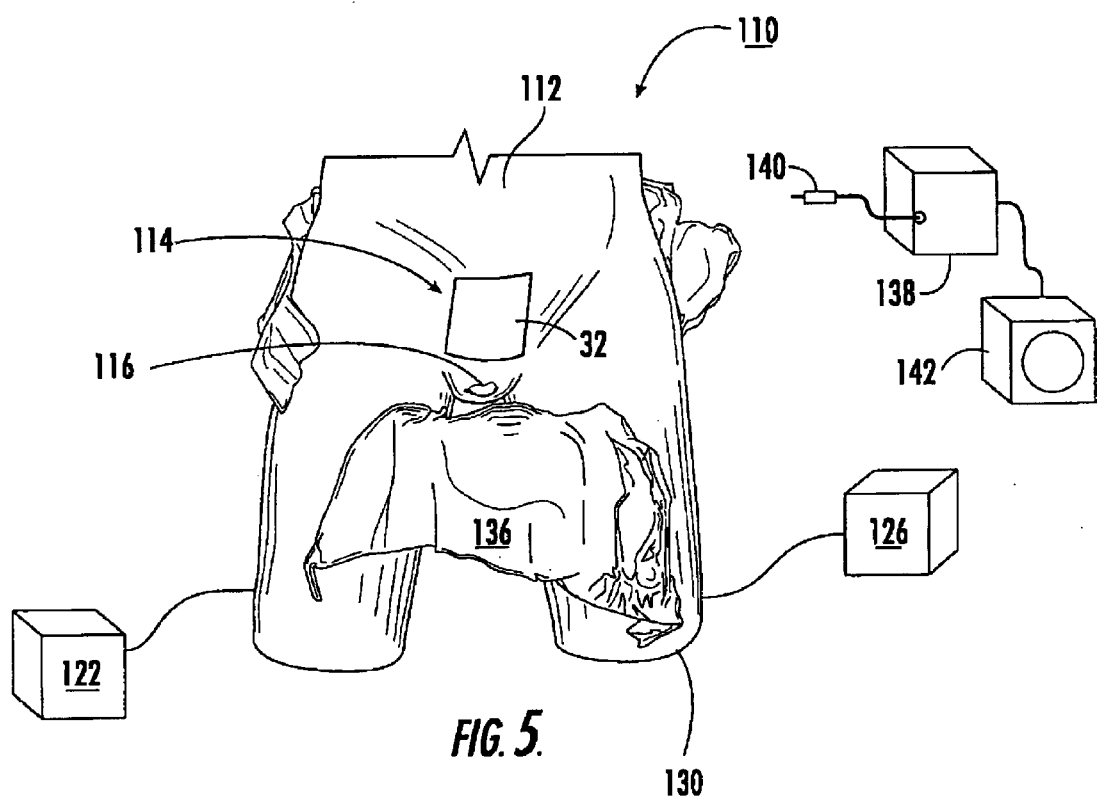
FIG. 5 is a perspective view of an evaluation apparatus in accordance with an aspect of the invention.
Figure 6:
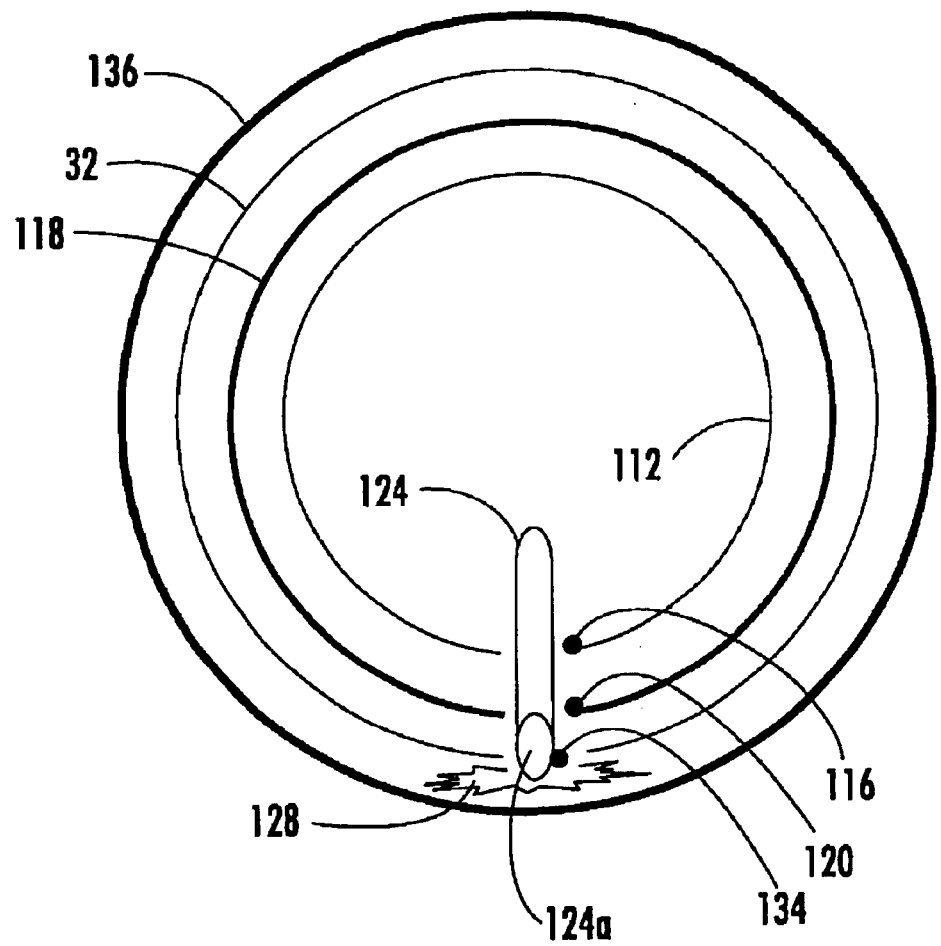
FIG. 6 is a cross-sectional plan view of a heated mechanical torso in accordance with a further aspect of the invention.

In another aspect of the invention broadly embodied in FIGS. 5 and 6, an evaluation apparatus 110 includes an object (torso) 112 and an artificial skin 132 similar to the skin 32 introduced above with respect to FIG. 2. The artificial skin 132 is attached to the torso 112 for testing a material 136. The material 136 is disposed about the skin 132, and a pump or fluid delivery device 126 is provided to insult the material 136 with a simulated physiological fluid 128 via a fluid injection port 116 in the torso 112. The fluid 128 may be water, saline, simulated menses fluid, simulated urine, artificial breast milk, blood, a solution of 0.9% sodium chloride, a colored solution, an exudate or any suitable material for simulating human body fluids. The foregoing arrangement facilitates skin dryness measurements using capacitance, conductance, electrical impedance, gravimetric, Trans-Epidermal Water Loss (TEWL), and other evaluations to measure skin hydration and moisturization. Material evaluators are thus able to rapidly pre-screen materials without the initial need for human subjects. Further details of the evaluation apparatus 110 and its operation are discussed below.

Referring to FIG. 5, there is shown a perspective view of one embodiment of the evaluation apparatus 110, which includes the torso 112 with the simulated skin 132 attached to an attachment area 114. As introduced, the simulated skin 132 can be at least partially covered with the material 136 that has been insulted with the fluid 128. Afterwards, the skin 132 is evaluated for wetness/dryness (TEWL) using the probe 140 of the measuring device 138 to prescreen the material 136.

In the example shown in FIG. 5, the torso 112 is formed of a silicone rubber material and is approximately the size of an infant. The torso 112 can be adjustably attached to the base 130 to facilitate the TEWL measurements that are described below. While the illustrated torso 112 is representative of an infant, it is not intended as a limitation of the invention. It is to be understood that other simulated anatomical parts representing, for instance, a man, woman, child, infant, or animal having other than the illustrated shape are within the scope of the invention. For example the torso 112 can be a mannequin selected from the group consisting of a lower-torso mannequin, an upper-torso mannequin, a full-body mannequin, a mannequin forearm, a mannequin hand, a mannequin foot, a mannequin leg, a mannequin head, and the like. Moreover, although the exemplary torso 112 is made of rubber, similar moldable materials such as acetyl plastic, an acrylic plastic, an elastomeric material, a high density polyethylene, a polymer, a metal, a glass, a composite material, or a Plexiglas® material may be used.

The fluid delivery device 126 shown in FIG. 5 is generally similar to the fluid delivery device 26 of the foregoing embodiment. FIG. 5 also shows a measuring device 138 similar to the previously described measuring device 38. Like probe 40 of measuring device 38, the measuring device 138 has a stand-mounted or hand-held probe 140 that can determine skin dryness, diaper pooling, skin saturation and the like by evaluating the skin 132 after insulting the material 136 with the fluid 128. Probe 140 can be a DermaLab® Trans-Epidermal Water Loss (TEWL) probe as described in the foregoing embodiment.

An electronic display unit or monitor 142, similar to previously introduced monitor 42, can be electronically attached to the measuring device 138 to display the TEWL measurements. The measuring device 138 and/or the monitor 142 can also include recording capabilities to automatically save the TEWL measurements to a magnetic tape, computer hard drive, disc or other recording medium.

FIG. 5 further shows an injection port 116 disposed in the attachment area 114. The material 136 is shown partially unfastened for clarity in the vicinity of the injection port 116. A tubing or fluid tube 124 (see FIG. 6) is located near the fluid injection port 116. The injection port 116 is sized and a fluid loading protocol used to simulate, for example, a child's model urine load, described in further detail below. In this exemplary arrangement, the tube 124 is routed within the apparatus 110 to ensure, for instance, that the tube 124 is not disturbed by external forces. However, it is to be noted that the tube 124 can be arranged to operate externally to the apparatus 110 without affecting an operation of the tube 124. It also is to be understood that the injection port 116 and the fluid tube 124 can vary in size and number. Likewise, various fluid loading protocols can be applied to model urination patterns of children, adults, animals and other various types of fluid excretions. For instance, an adult incontinence product insult may be 105 milliliters (ml) to at least 480 ml. The protocol for insulting 105 ml or 480 ml are as follows: 3 leadings of 35 ml, 45 seconds apart, at 6 ml/sec (105 ml total) and 3 loadings of 75 ml, 15 minutes apart at 8 ml/sec (total of 480 ml for a large size product).

Referring to FIG. 6, a cross sectional view of the torso 112 is shown. The fluid tube 124 is inserted through the fluid injection port 116 of the torso 112. The heater 118 has a heater hole 120 through which the fluid tube 124 is also at least partially inserted. In this example, the heater 118 is a network of heating elements embedded in the silicone rubber torso 112. The heater 118 may, however, be an external heater that is wrapped around or attached to the attachment area 114 and connected to an electrical connection or power source 122 (see FIG. 5). If an external attachable heater 118 is selected, it is fashioned from a flexible silicone rubber, neoprene or other flexible material and is designed for removable attachment to the apparatus 110. A detachable heater suitable for use with the exemplary torso 112 is available from Watlow Electric Manufacturing Company of St. Louis, Mo.; however, comparable heaters from other manufacturers can be substituted.

To simulate normal human skin temperature, the heater 118 is heated from about 70° Fahrenheit (F.) to about 120° F. via the power source 122 to heat the skin 132. However, the heater 118 is normally programmed at about 95° F. to emulate a surface temperature of normal human skin. Heating the skin 132 with the heater 118 facilitates correlation of the present invention to the conventional Adult Forearm Test in order to better support, for instance, advertising claims, develop products and similar endeavors. More specifically, when the skin 132 is heated to about 85–99° F. rather than remaining at an ambient room temperature, the TEWL measurements more closely reflect measurements that are normally taken from a human forearm and to better differentiate products. The operation of the heater 118 and resulting TEWL measurements are described in the Exemplary Procedures and Exemplary Results sections below.

With further reference to FIG. 6, the fluid tube 124 is placed near the skin 132, which may have a skin opening 134. The skin opening 134 and an insult source (outlet) 124a of the tube 124 simulate a human urethra and cooperate to direct the fluid 128 into the material 136, such as a diaper. The material 36 is placed about the skin 132 to be insulted with fluid 128 as introduced above. In this example, the fluid tube 124 (and skin opening 134 if provided) is aligned substantially with the heater hole 120. In this example, the previously described fluid loading protocol simulating a child's model urine load is used. It is to be understood that the outlet 124a and skin opening 134 can vary in size and number to simulate tear ducts, pores, body cavity, urethra, and similar openings. Additionally, various other fluid loading protocols can be utilized to model infant urination, adult perspiration menses, synthetic breast milk and blood such as bovine blood, or other fluid excretions.

Although skin 132 is shown wrapped around the heater 118 in FIG. 6, it is to be understood that the skin 132 may be a small patch or square of skin 132 relative to the heater 118 as seen in FIG. 5. The small patch of skin 132 is placed at pre-selected distances from the injection port 116. For example, research has shown that 6 centimeters (cm) is an advantageous distance from the injection port 116 to the skin 132. Using VITRO-SKIN™ as the skin 132, the inventors have found through placing the skin 132 at various locations on the torso 112 fewer differences are detectable when the simulated skin 132 is placed closer to the injection port 116. Stated another way, although distances of about zero cm to about 12 cm are feasible, TEWL measurements may undesirably vary or be difficult to differentiate when the skin 132 is too close to the injection port 116 and a transmission or surge area of the fluid 128.

In operation, the material 136 (seen partially detached for clarity in FIG. 5) is securely wrapped about the torso 112 to at least partially cover the skin 132. The fluid delivery device 126 delivers the fluid 128 through the injection port 116 into the material 136 for TEWL or other evaluation as more particularly described in the following protocols and experiments.

I. Experiment Conducted on an Exemplary Embodiment of the Invention

Results derived from experiments conducted in accordance with one exemplary embodiment of the present invention are as follows. In the following hydration experiment, a diaper was tested on the evaluation apparatus 10 illustrated in FIGS. 1 and 4.

In this experiment, a Step 3 Ultra-Trim® diaper was used as the material or diaper 36. The diaper 36 was attached about the arm 12 proximate the attachment area 14. The digital pump 26, capable of less than 1 cubic centimeters per minute (cc/min) to over 800 cc/min was set to insult 60 cc/min of simulated physiological fluid or warmed saline 28 in 12 seconds. The digital pump 26 was further programmed to insult the diaper 36 with saline 28 three times. The diaper 36 was marked with a target measurement zone (not shown) 15.2 cm from the top front of the diaper 36 on its inside. The back of the diaper 36 was marked on its outside approximately 5 cm from the top. The target-loading zone should be measured and marked 21.2 cm from the top front of the diaper 36. The target loading zone was lined up directly under the tube 24 on the under side of the arm 12 with the front of the diaper 36 at the top. The back of the diaper 36 was wrapped around the arm 12 and securely taped with the back of the diaper 36 located on the top of the arm and folded to the inside at the 5 cm mark. The diaper 36 was insulted with the saline 28 three times and evaluated after 30–90 minutes.

Result: After 30–90 minutes, the evaluation apparatus 10 was used successfully to measure the skin 32.

II. Experiment Conducted on Another Exemplary Embodiment of the Invention

Exemplary Procedure

Results derived from experiments conducted in accordance with another exemplary embodiment of the present invention are as follows. In this experiment with particular reference to FIG. 4, the following test procedure employed a diaper 36 tested on the mechanical arm 12:

1. Preheat the mechanical arm (12) to 95° F. before beginning.
2. Turn on the computer (38) and DermaLab® instrument (40). Warm up according to manufacturer's directions.
3. Turn on the fluid delivery device (26).
4. Calibrate the fluid delivery device (26) prior to use.
5. Measure and mark TEWL measurement zone 15.2 cm from the top inside edge of a Step 3 Ultra-Trim® diaper (36).
6. Measure and mark Loading Zone—21.2 cm from the top inside edge of the Ultra-Trim® diaper (36).
7. Using an unused piece or patch (32) of simulated skin—for this experiment, a 5 cm×3.8 cm patch of VITRO-SKIN™ was used—place it securely on the side of the mechanical arm (12) using waterproof surgical tape. The VITRO-SKIN™ should be on the side facing the experimenter (rough side out), approximately 0.75 cm from the top of the heating element (not shown).
8. Place the diaper (36) on the arm (12) with the front waistband facing the experimenter. Align the TEWL measurement zone (15.2 cm) on the diaper (36) with the patch (32). The diaper (36) should be wrapped down and around the arm (12) with the back of the diaper (36) slightly folded. The front waistband wraps slightly over the back. Ensure that the loading tube (24) embedded in the arm (12) lines up with the loading zone on the diaper (36). The diaper (36) is secured on the arm (12) by masking tape. The tape is tightly wrapped around both ends of the diaper (36).
9. Use program 3S300T45 on the computer in the WINLIN software. Press start to begin the loading procedure. 60 milliliter/second (mls) of saline (28) should begin to flow into the diaper (36) at 300 cc/mm every 45 seconds, three times or a total load of 180 mls.

10. After the third and final insult, set and start a timer for 60 minutes.
11. After 60 minutes, open the diaper (36) and quickly remove the patch (32) from the arm (12) and place the patch (32) on a cosmetic sponge (not shown) for a TEWL measurement.
12. Record the TEWL measurement in a notebook, and save it to a Microsoft® Excel file.

Exemplary Results

The initial TEWL value for the patch (32) prior to use on the arm (12) was zero $g/m^2/hr$. The patch (32) was conditioned in a controlled laboratory setting at 72° Fahrenheit +/−2° Fahrenheit, 40% RH +/−5%. Typically, a baseline TEWL measurement is taken on human skin prior to conducting known Clinical Research Service (CRS) Adult Armband Testing. The baseline value is then subtracted from the final TEWL value for a trans-epidermal water loss measurement in units of $g/m^2/hr$. For this experiment, since the initial TEWL value was zero $g/m^2/hr$, no subtraction was necessary. It is to be noted that in the foregoing exemplary experiment, 60 mls of saline was insulted at 300 cc/min every 45 seconds. However, other protocols ranging, for example, between about 10 cc/min to about 800 cc/min for 10–60 seconds can be used to simulate other human age groups.

A strong correlation was shown between the CRS Armband Test versus this exemplary experiment ($R^2$=0.958). This indicates that using a mechanical apparatus as a screening tool for materials and components of products is effective and practical.

Moreover, in a small-scale study two groups of diapers 36, each numbering ten diapers, were evaluated three weeks apart using the foregoing protocol with no significant differences detected between the two groups of diapers 36 from the same bag and lot number. The study therefore shows that the testing is repeatable with at least a 95% confidence level.

Based on the strong correlation between the CRS Armband Test and this mechanical experiment and its repeatability, the experiment can be used as a bench test for evaluating test equipment and pre-screening materials for skin dryness for use in final product testing. However, it is to be understood that the experiment may also be used to screen competitive products, perform other research and development and the like and is not limited to the foregoing exemplary uses.

III. Experiment Conducted on Another Exemplary Embodiment of the Present Invention Results derived from experiments conducted in accordance with one exemplary embodiment of the present invention are as follows. In this experiment with particular reference to FIGS. 5 and 6, the following test procedure employed a diaper 136 tested on the mannequin torso 112:

Exemplary Procedure

1. Preheat the mannequin (112) to 94° Fahrenheit and saline (128) to 35° C. (95° F.).
2. Turn on the computer (138) and DermaLab® instrument (140). Warm up according to manufacturer's directions.
3. Loading Zone—measure and mark 21.2 cm from the top inside edge of an Ultra-Trim® diaper (136).
4. Take the mannequin (112) off the stand (not shown) and lay on its back.
5. Check position of the saline tube (124). Ensure it has not moved and is located inside at the center rear opening of the mannequin (112).
6. Position the diaper (136) under the mannequin (112).
7. Using an unused piece or patch (132) of simulated skin—for this experiment, a 2"×1.5" patch of VITRO-SKIN™ was used—position the patch (32) on the front of the mannequin (112). The patch (132) will be centered on the mark (not shown) on the mannequin (112), approximately 8.57 cm from the center of the saline loading tube (124) to the center of the patch (132). The rough side of the patch (132) must be up. Tape is not needed.
8. Place the diaper on the mannequin (112) with the front waistband facing the experimenter. Align the TEWL measurement zone (15.2 cm) on the diaper (136) with the patch (132). Ensure that the loading tube (124) embedded in the mannequin (112) lines up with the loading zone on the diaper (136).
9. Close the diaper (136).
10. Replace the mannequin (112) on its stand.
11. Insult the diaper (136) with the saline (128) three times, 60 milliliters per second (mls) each time, with a fluid delivery device (not shown). The saline (128) is warmed to 35° C. prior to insulting the diaper (136). The insults should be 45 seconds apart.
12. After the third and final insult, set and start a timer for 60 minutes.
13. After 60 minutes, open the diaper (136) and quickly remove the patch (132) from the mannequin (112) and place it on a cosmetic sponge (not shown) for a TEWL measurement.
14. Take a TEWL measurement on the center of the patch (132).
15. Record the TEWL output in a notebook, and save same to a Microsoft® Excel file.

Exemplary Results

The initial TEWL value for the patch (132) prior to use on the mannequin (112) was zero $g/m^2/hr$. The patch (132) was conditioned in a controlled laboratory setting at 72° Fahrenheit +/−2° Fahrenheit, 40% RH +/−5%. Typically, a baseline TEWL measurement is taken on human skin prior to conducting known Clinical Research Service (CRS) Adult Armband Testing. The baseline value is then subtracted from the final TEWL value for a trans-epidermal water loss measurement in units of $g/m^2/hr$. For this experiment, since the initial TEWL value was zero $g/m^2/hr$, no subtraction was necessary. It is to be noted that although 60 mls was insulted three times, 45 seconds apart, other protocols can be substituted to simulate other human age groups. For example, saline can be insulted at between about 10 cc/min to about 800 cc/min for 10–60 seconds at various intervals.

A strong correlation was shown between the CRS Armband Test versus this exemplary experiment ($R^2$=0.952). This indicates that using a mechanical apparatus as a screening tool for materials and components of products is practical.

Moreover, in a small-scale study two groups of diapers 136, each numbering ten diapers, were evaluated three weeks apart using the foregoing protocol with no significant differences detected between the two groups of diapers 136 from the same bag and lot number. The study therefore shows that the testing is repeatable with at least a 95% confidence level.

Based on the strong correlation between the CRS Armband Test and the mechanical torso experiment and its repeatability, the torso can be used as a bench test for evaluating test equipment and pre-screening materials for skin dryness for use in final product testing. However, it is to be understood that the experiment may also be used to screen competitive products, perform other research and development and the like and is not limited to the foregoing exemplary uses.

IV. Experiment Conducted on a Further Exemplary Embodiment of the Present Invention Exemplary Procedure Results derived from experiments conducted in accordance with another exemplary embodiment of the present invention are as follows. In this experiment with particular reference to FIG. 4, the following test procedure employed a diaper 36 tested on the mechanical arm 12:

1. An acrylic tube or "arm" 12 having an outer diameter of 3.25 inches (8.25 cm) was mounted onto a stand 30 parallel to the ground.

2. A piece of VITRO-SKIN™ (6.5 cm by 6.5 cm) of formulation 5X-2G-19 is used as skin 32. The skin 32 is weighed and taped to the arm 12 using scotch tape.

3. A Step 3 size Huggies® Ultratrim diaper 36 is wrapped around the arm 12 as would be done in an armband TEWL study, with the target on the bottom side of the arm 12 at the point of fluid introduction.

4. The diaper 36 is secured around the arm 12 with masking tape.

5. Three insults of 60 ml of saline are introduced into the diaper 36, between the skin 32 and the diaper 36, at a rate of 5 cc/sec at 45 second intervals.

6. The diaper 36 remains on the arm 12 for 1 hour after the final insult.

7. After the diaper 36 is removed, the skin 32 is weighed again.

8. A difference in weights is calculated and normalized to the area of the skin 32.

9. Results are reported in $g/m^2/hr$ and are referred to as pick-up values.

Products that have been tested in armband TEWL were also tested with this test method. The present test has been used to distinguish between the poor and the good performing products. For example, a knit polyester liner of 220 denier fibers that has been thermoformed with ¼ inch bumps consistently performs better than a standard diaper liner in an armband TEWL with up to a 40% TEWL reduction.

The knit polyester liner also performed better than standard diaper liner with this experimental test method. Specifically, a 38% decrease in pick-up from the control was measured with the knit liner. The control product, or standard Huggies® Ultratrim diaper liner, had a pick-up of 91 $g/m^2/hr$ with a standard deviation of 14. The knit polyester liner had a measured pick-up of 56 $g/m^2/hr$ with a standard deviation of 5. Both products were tested with a sample size of 3. The percentage decrease measured with the experimental test method does not match the decrease in armband TEWL, but shows a directional relationship.

It is to be understood that the above exemplary values are not intended as limitations of the invention. For instance, the substrate can be sized from about 2 $cm^2$ to about 100 $cm^2$. Additionally, the fluid can be insulted in the material from about 45 ml to about 250 ml at a rate of about 1 cc/sec to about 15 cc/sec and at about 30 second intervals to about 60 minute intervals. Furthermore, the fluid-insulted material can be left on the artificial arm for about 30 minutes to about 5 hours, more particularly about 1 hour after a final insult.

The foregoing test method illustrates that materials and products can be ranked using an artificial arm and simulated skin substrate with similar results to armband TEWL rankings. In other words, this method can be used to prescreen any materials and systems that are presently tested with TEWL. It is also to be noted that this method is applicable to infant, child, and adult care products.

While preferred embodiments of the invention have been shown and described, those skilled in the art will recognize that other changes and modifications may be made to the foregoing embodiments without departing from the spirit and scope of the invention. For example, specific shapes of various elements of the illustrated embodiment may be altered to suit particular applications such as shaping the object 12 as a lower torso mannequin, an upper torso mannequin, a full body mannequin, a mannequin forearm, a mannequin hand, a mannequin foot, a mannequin head and various other portions of a human body. It is intended to claim all such changes and modifications as fall within the scope of the appended claims and their equivalents.

That which is claimed is:

1. An apparatus for evaluating a material insulted with a fluid, the apparatus comprising:

an adjustable object with an arcuate surface defining a circumference, the arcuate surface configured for adjustment of the circumference to accommodate a material disposed on the arcuate surface, the material ranging in size from a diaper to an adult undergarment;

a substrate attached to the arcuate surface of the adjustable object; and means for injecting simulated human fluid into the material contactable with the substrate, the adjustable object configured to position the substrate for evaluation.

2. The apparatus as in claim 1, wherein the material is an absorbent article selected from the group consisting of disposable or non-disposable feminine products, nursing healthcare products, disposable or non-disposable child training pants, face masks, bandages, gloves and combinations thereof.

3. The apparatus as in claim 1, wherein the simulated human fluid is selected from the group consisting of water, saline, synthetic menses, synthetic urine, artificial breast milk, blood, 0.9% sodium chloride solution, colored solution, exudate and combinations thereof.

4. The apparatus as in claim 1, wherein the object is selected from the group consisting of a lower-torso mannequin, an upper-torso mannequin, a full-body mannequin, a mannequin forearm, a mannequin hand, a mannequin foot, a mannequin leg, a mannequin head, and combinations thereof.

5. The apparatus as in claim 1, wherein the object is formed of a silicone, a neoprene, a plastic, an acetyl plastic, an acrylic plastic, an elastomeric material, a high density polyethylene, a polymer, a metal, a glass, a composite material and combinations thereof.

6. The apparatus as in claim 1, further comprising a fluid delivery device and a tubing in communication with the adjustable object, the tubing having an opening terminating at a fluid injection port defined in the adjustable object, the fluid delivery device and the tubing cooperably configured to insult a predetermined amount of the simulated human fluid through the fluid injection port.

7. The apparatus as in claim 1, further comprising a fluid delivery device, wherein the fluid delivery device is a digital pump in communication with an embedded tubing within the adjustable object, the embedded tubing having an opening terminating at a fluid injection port of the adjustable object, the digital pump and the embedded tubing cooperably configured to insult a predetermined amount of the simulated human fluid through the fluid injection port.

8. The apparatus as in claim 1, further comprising a measuring device configured to measure a condition of the substrate.

9. The apparatus as in claim 1, wherein the adjustable object is adjusted by one of swiveling, rotating, retracting, extending, ratcheting, inclining, reclining, and combinations thereof.

10. The apparatus as in claim 1, wherein a circumference of the adjustable object is adjustable by one of electrical, hydraulic, pneumatic, and manual adjustment.

11. The apparatus as in claim 8, wherein the measuring device is configured to record the condition of the substrate.

12. The apparatus as in claim 8, wherein the measuring device measures the condition of the substrate by one of capacitance, conductance, electrical impedance, gravimetric and TEWL evaluations.

13. The apparatus as in claim 8, further comprising a monitor in electrical communication with the measuring device, the monitor configured to display the condition of the substrate.

\* \* \* \* \*

UNITED STATES PATENT AND TRADEMARK OFFICE
CERTIFICATE OF CORRECTION

PATENT NO. : 6,931,951 B2
APPLICATION NO. : 10/324884
DATED : August 23, 2005
INVENTOR(S) : Wright et al.

It is certified that error appears in the above-identified patent and that said Letters Patent is hereby corrected as shown below:

On page 2, 2nd column, IDS Reference 6,503,525 B1, delete --Mayberry et al.-- and insert "Paul et al."

Signed and Sealed this

First Day of August, 2006

JON W. DUDAS
*Director of the United States Patent and Trademark Office*